(12) United States Patent
Yang et al.

(10) Patent No.: US 10,864,169 B2
(45) Date of Patent: Dec. 15, 2020

(54) CONJUGATED POLYMER NANOPARTICLES AND MANUFACTURING METHOD THEREOF

(71) Applicant: Industry-Academic Cooperation Foundation, Yonsei University, Seoul (KR)

(72) Inventors: Jae Moon Yang, Seoul (KR); Jung Hyun Kim, Seoul (KR); Jeong Hun Kim, Seoul (KR); Yoo Chan Hong, Seoul (KR); Won Seok Cho, Seoul (KR); Seung Yeon Hwang, Seoul (KR); Jin Suck Suh, Seoul (KR)

(73) Assignee: Industry-Academic Cooperation Foundation, Yonsei University, Seoul (KR)

( * ) Notice: Subject to any disclaimer, the term of this patent is extended or adjusted under 35 U.S.C. 154(b) by 142 days.

(21) Appl. No.: 15/505,036

(22) PCT Filed: Mar. 19, 2015

(86) PCT No.: PCT/KR2015/002667
§ 371 (c)(1),
(2) Date: Feb. 17, 2017

(87) PCT Pub. No.: WO2016/027952
PCT Pub. Date: Feb. 25, 2016

(65) Prior Publication Data
US 2017/0266124 A1  Sep. 21, 2017

(30) Foreign Application Priority Data
Aug. 20, 2014 (KR) .................. 10-2014-0108410

(51) Int. Cl.
| | | |
|---|---|---|
| A61K 31/704 | (2006.01) |
| A61K 9/51 | (2006.01) |
| A61K 49/00 | (2006.01) |
| A61K 41/00 | (2020.01) |
| A61K 47/34 | (2017.01) |

(52) U.S. Cl.
CPC .......... *A61K 9/5146* (2013.01); *A61K 9/513* (2013.01); *A61K 9/5123* (2013.01); *A61K 9/5192* (2013.01); *A61K 31/704* (2013.01); *A61K 41/0028* (2013.01); *A61K 41/0052* (2013.01); *A61K 47/34* (2013.01); *A61K 49/00* (2013.01); *A61K 49/0054* (2013.01); *A61K 49/0093* (2013.01)

(58) Field of Classification Search
None
See application file for complete search history.

(56) References Cited

U.S. PATENT DOCUMENTS

| | | | | |
|---|---|---|---|---|
| 5,281,363 A * | 1/1994 | Shacklette | ......... | C08G 73/0266 252/500 |
| 6,117,454 A * | 9/2000 | Kreuter | ............... | A61K 9/5138 424/489 |
| 8,476,242 B2 * | 7/2013 | Mon | .................. | A61B 18/1477 424/93.1 |
| 2007/0264199 A1 * | 11/2007 | Labhasetwar | ........ | A61K 9/5094 424/9.32 |
| 2009/0263359 A1 * | 10/2009 | Ferreira | .............. | C12N 5/0619 424/93.7 |
| 2011/0027172 A1 * | 2/2011 | Wang | .................. | A61K 31/337 424/1.29 |

FOREIGN PATENT DOCUMENTS

| | | | |
|---|---|---|---|
| CN | 102432876 B | * | 7/2014 |
| KR | 20090113990 A | | 11/2009 |
| KR | 20120107686 A | | 10/2012 |
| KR | 101267313 B1 | * | 5/2013 |

OTHER PUBLICATIONS

Sinha et al (Journal of Applied Polymer Science, 112, 3135-3140, 2009). (Year: 2009).*
Choi, J. et al., "Redox-sensitive colorimetric polyaniline nanoprobes synthesized by a solvent-shift process", Nano Research, 2013, vol. 6, No. 5, pp. 356-364.
Zhang, L. et al., "Polyaniline micro/nanofibers doped with saturation fatty acids", Synthetic Metals, 2006, vol. 156, pp. 454-458.
Song, E. et al., "Conducting polyaniline nanowire and its applications in chemiresistive sensing", Nanomaterials, 2013, vol. 3, pp. 498-523.
Augustine, M. S. et al., "Enhanced photoluminescence in oleic acid modified polyaniline", Transactions of The Indian Institute of Metals, 2011, vol. 64, Nos. 1-2, pp. 209-212.
International Search Report for International Application No. PCT/KR2015/002667, dated Jun. 30, 2015.
International Preliminary Report on Patentability, Corresponding International Application No. PCT/KR2015/002667, dated Feb. 21, 2019.
Written Opinion of the International Searching Authority, corresponding International Application No. PCT/KR2015/002667, dated Jun. 30, 2015. (English Translation).

* cited by examiner

*Primary Examiner* — Celeste A Roney
(74) *Attorney, Agent, or Firm* — Marshall, Gerstein & Borun LLP

(57) ABSTRACT

Disclosed are conjugated polymer nanoparticles and a method of producing the same. The conjugated polymer nanoparticles include a conjugated polymer, fatty acid and an amphiphile polymer. The conjugated polymer nanoparticles can be doped even under a neutral environment, thus exhibiting high electrical conductivity and exerting absorbance properties in the near-infrared band even under a neutral environment such as in vivo.

12 Claims, 4 Drawing Sheets

CONJUGATED POLYMER NANOPARTICLES AND MANUFACTURING METHOD THEREOF

CROSS REFERENCE TO RELATED APPLICATIONS

This application is the U.S National Phase of International Patent Application No. PCT/KR2015/002667 filed Mar. 19, 2015, which claims the benefit of Korean Patent Application No. 10-2014-0108410 filed Aug. 20, 2014, the respective disclosures of which are each incorporated herein by reference in their entireties.

BACKGROUND

Technical Field

The present invention relates to conjugated polymer nanoparticles and a method of producing the same. More particularly, the present invention relates to conjugated polymer nanoparticles which are useful for accurate drug delivery to local sites, disease diagnosis, disease treatment, near-infrared imaging and photothermal therapy, and a method of producing the same.

Background Art

Since the fact that electricity can be conducted by treating conjugated polymers such as polyacetylene with chlorine, bromine, iodine gas or the like was discovered, conjugated polymers have been actively researched as conductive polymers. In practice, conjugated polymers have been widely used as antistatic, electromagnetic shielding and electrode materials and the like. Currently, in addition to polyacetylene, a variety of conjugated polymers are developed and used.

Methods of producing conjugated polymers are well-known. For example, in accordance with Korean Patent Laid-open No. 2012-0107686, conjugated polymers can be produced by chemical oxidative polymerization.

In order to use the conjugated polymers for sensors, bioprobes and the like, it is necessary to produce conjugated polymer nanoparticles having a structure in which an amphiphile compound surrounds a conjugated polymer. Solvent evaporation was widely used as a method of producing such conjugated polymer nanoparticles. The solvent evaporation includes dissolving a conjugated polymer in an organic solvent such as chloroform or hexane, emulsifying the resulting solution and evaporating the organic solvent. However, the solvent evaporation may have a drawback of poor biocompatibility because of use of a solvent insoluble in water, requires additional energy for emulsification, offers a relatively large particle size of nanoparticles and has a disadvantage of difficulty in mass-production.

In addition, the conjugated polymer produced by the method exhibits electrical properties and absorption characteristics in near-infrared areas when they are doped under only a strong acid (pH 2 or less) environment. Accordingly, such a conjugated polymer has a problem of low applicability under a neutral environment such as in vivo, not a strong acid environment.

Patent Document 1: Korean Patent Laid-open No. 2012-0107686 (published on Oct. 4, 2012)
Patent Document 2: Korean Patent Laid-open No. 2009-0113990 (published on Nov. 3, 2009)

SUMMARY

Therefore, the present invention has been made in view of the above problems, and it is one object of the present invention to provide conjugated polymer nanoparticles which can be doped under a neutral environment and can thus exert high electrical conductivity and excellent absorption properties in near-infrared areas under a neutral environment such as in vivo.

It is another object of the present invention to provide a method of producing conjugated polymer nanoparticles which are doped even under a neutral environment.

In accordance with the present invention, the above and other objects can be accomplished by the provision of conjugated polymer nanoparticles including a conjugated polymer, fatty acid and an amphiphile polymer.

The conjugated polymer nanoparticles may include 1 to 1,000 parts by weight of the fatty acid and 1 to 1,000 parts by weight of the amphiphile polymer, with respect to 100 parts by weight of the conjugated polymer.

The fatty acid may include any one selected from the group consisting of oleic acid, capric acid, caprylic acid, palmitic acid, lauric acid, myristic acid, arachidic acid, behenic acid, lignoceric acid, cerotic acid and a combination thereof.

The amphiphile polymer may include any one selected from the group consisting of a cationic surfactant, an anionic surfactant, an amphoteric surfactant, a nonionic surfactant and a mixture thereof.

The amphiphile polymer may include any one selected from the group consisting of sodium cholate hydrate, n-octyl glucoside, octyl thioglycoside, N-octanoyl-N-methylglucamine, N-nonanoyl-N-methylglucamine, quillaja bark-derived saponin, polyoxyethylene sorbitan monolaurate, sodium dodecyl sulfate, tetramethylammonium hydroxide solution, hexadecyltrimethylammonium bromide (CTAB), didodecyldimethylammonium bromide (DMAB), N,N-bis (3-D-glucoamidopropyl)deoxy-cholamide (deoxy-BIG-CHAP), N,N-bis(3-D-glucoamidopropyl)cholamide (BIG-CHAP), polyvinyl alcohol, polyethylene glycol dodecyl ether, Pluronic F-68, Triton X-100, Triton X-114, Tween 40, Tween 80, Igepal CA-630, Igepal CO-210, Igepal CO-520, Igepal CO-630, Igepal CO-720, Igepal CO-890, Igepal DM-970, Igepal CA-210, Igepal CA-520, Igepal CA-630, N-decanoyl-N-methylglucamine, nonylphenyl polyethylene glycol, Brij 76, Brij 58, Brij 35P, Brij 30, Polysorbate 80, cyclohexylmethyl-β-D-maltoside (Cymal-1), 2-cyclohexylethyl-β-D-maltoside (Cymal-2), 5-cyclohexylpentyl-β-D-maltoside (Cymal-5), 6-cyclohexylhexyl-β-D-maltoside (Cymal-6), digitonin, decyl-β-D-maltopyranoside, lauryl-β-D-maltoside (DDM), n-hexadecyl-β-D-maltoside, undecyl-β-D-maltoside, decyl-β-D-1-thiomaltopyranoside, decyl-β-D -1-thioglucopyranoside, dimethyldecylphosphine oxide, dodecyldimethylphosphine oxide and a mixture thereof.

The conjugated polymer may include any one selected from the group consisting of polyacetylene, polyaniline, polypyrrole, polythiophene, poly(1,4-phenylenevinylene), poly(1,4-phenylene sulfide), poly(fluorenyleneethynylene), a derivative thereof and a mixture thereof.

The conjugated polymer nanoparticles may include a core including the conjugated polymer and the fatty acid, and a shell surrounding the core and including the amphiphile polymer.

The core may further include a pharmaceutically active ingredient.

The conjugated polymer nanoparticles may include 0.1 to 100 parts by weight of the pharmaceutically active ingredient, with respect to 100 parts by weight of the conjugated polymer.

The pharmaceutically active ingredient may include any one selected from the group consisting of anticancer agents, antibiotics, hormones, hormone antagonists, interleukins, interferons, growth factors, tumor necrosis factors, endotoxins, lymphotoxins, urokinase, streptokinase, tissue plasminogen activators, protease inhibitors, alkylphosphocholine, radioisotope-labeled molecules, cardiovascular drugs, gastrointestinal drugs and neurological drugs.

The conjugated polymer of the conjugated polymer nanoparticles may be doped at pH 1 to 8 with a dopant.

The conjugated polymer nanoparticles may have a diameter of 1 to 500 nm.

In another aspect of the present invention, provided is a method of producing conjugated polymer nanoparticles including dissolving a conjugated polymer and fatty acid in a solvent to prepare a first mix solution, mixing the mix solution with a solution containing an amphiphile polymer to prepare a second mix solution, and conducting reaction of the second mix solution.

The preparing the first mix solution may include further adding a pharmaceutically active ingredient.

The solvent may include any one selected from the group consisting of N-methyl-2-pyrrolidone, acetone, acetonitrile, carbon tetrachloride, chloroform, cyclohexane, 1,2-dichloroethane, dichloromethane, diethyl ether, dimethyl formamide, dimethyl sulfoxide, 1,4-dioxane, ethanol, ethyl acetate, heptane, hexane, methanol, methyl tert-butyl ether, pentane, 1-propanol, 2-propanol, tetrahydrofuran, toluene, 2,2,4-trimethylpentane, water and a mixture thereof.

The reaction of the second mix solution may be conducted by stirring the second mix solution at a temperature lower than or equal to a melting point of the fatty acid.

ADVANTAGEOUS EFFECT

The conjugated polymer nanoparticles of the present invention can be doped under a neutral environment, and thus can exert electrical conductivity and excellent absorbance properties in the near-infrared band even under a neutral environment such as in vivo. As a result, when the conjugated polymer nanoparticles are loaded in drugs, the loaded drugs can be realized by inducing local temperature change by laser, so that accurate drug delivery to local sites, disease diagnosis, disease treatment, near-infrared imaging and photothermal therapy are possible.

Using the method of producing conjugated polymer nanoparticles of the present invention, conjugated polymer nanoparticles doped under a neutral environment can be produced.

BRIEF DESCRIPTION OF THE DRAWINGS

The above and other objects, features and other advantages of the present invention will be more clearly understood from the following detailed description taken in conjunction with the accompanying drawings, in which.

DETAILED DESCRIPTION

Figure 1:
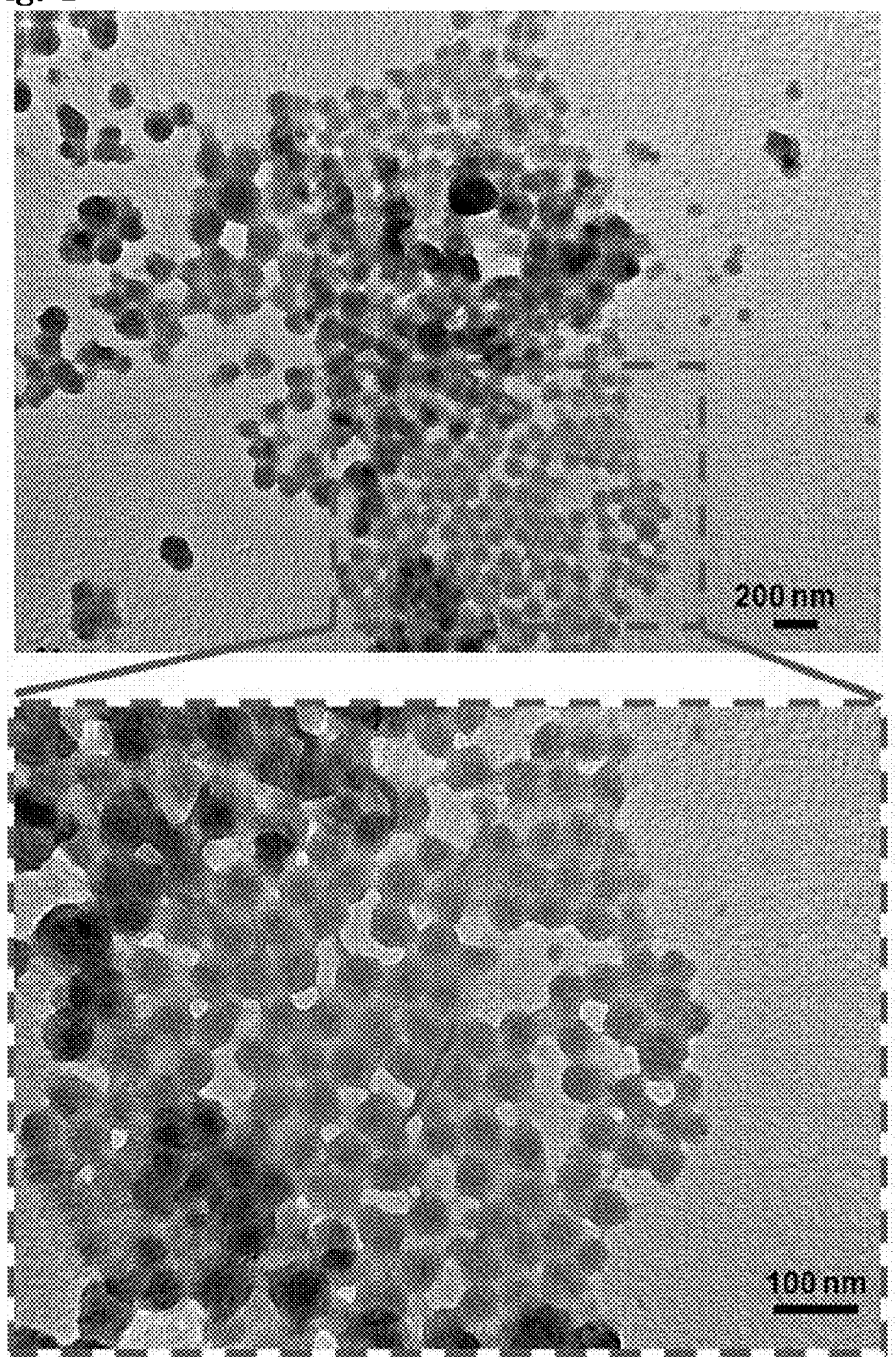
FIG. 1 is a transmission electron microscope (TEM; JEM-1011 JEOL, Japan) image of polyaniline nanoparticles produced in Example 1.

Hereinafter, preferred embodiments of the present invention will be described in detail such that they can be easily implemented by a person having ordinary knowledge in the art. However, the present invention can be implemented by a variety of different embodiments and should be construed as being limited to the embodiments described herein.

The conjugated polymer nanoparticles according to an embodiment of the present invention include a conjugated polymer, fatty acid and an amphiphile polymer.

Any conductive polymer can be used without limitation so long as it can exert electrical conductivity by doping with a dopant. The kinds of the conjugated polymers possessing this property are well-known. The conjugated polymer is selected from the group consisting of polyacetylene, polyaniline, polypyrrole, polythiophene, poly(1,4-phenylenevinylene), poly(1,4-phenylene sulfide), poly(fluorenylene-ethynylene), derivatives thereof and mixtures thereof, but the present invention is not limited thereto.

In a specific embodiment of the present invention, the conjugated polymer may be polyaniline. The polyaniline has excellent biocompatibility and is applicable as an electrically active material for cell proliferation research. In addition, polyaniline is a dopant (for example, strong acid, Lewis acid, transition metal, alkali ion) for quantization which induces electron transfer and leads to a band gap between a valence band and a conduction band reducing an excitation-energy level. Accordingly, the optical absorption peak of polyaniline shifts from emeraldine base (EB) to emeraldine salt (ES) during doping and redshift to a near-infrared area happens.

The conjugated polymer nanoparticles include fatty acid as well as the conjugated polymer so that they can be doped with a dopant even under a neutral environment. Accordingly, the conjugated polymer nanoparticles can exert high electrical conductivity and excellent absorption properties in near-infrared areas even under a neutral environment such as in vivo. As a result, when the conjugated polymer nanoparticles are loaded in drugs, the nanoparticle-loaded drugs can be released by inducing local temperature variation using a laser, so that accurate drug delivery to local sites, disease diagnosis, disease treatment, near-infrared imaging and photothermal therapy are possible.

The fatty acid may be saturated fatty acid or unsaturated fatty acid, is preferably C8 to C30 fatty acid, and is for example selected from the group consisting of oleic acid, capric acid, caprylic acid, palmitic acid, lauric acid, myristic acid, arachidic acid, behenic acid, lignoceric acid, cerotic acid and a combination thereof.

In addition, the fatty acid is a phase change material which is present in a solid phase during the production of the conjugated polymer nanoparticles and can be melted by heat emitted from the conjugated polymer absorbing light upon irradiation of a laser in vivo.

That is, by using fatty acid among phase change materials, the conjugated polymer can be doped, especially, under a neutral environment as well as under an alkaline environment of pH 8 or less, preferably of pH 1 to 8, without an additional doping process.

The dopant useful for doping the conjugated polymer may include at least one oxide material or bio-molecule having an oxidation/reduction potential selected from the group consisting of active oxygen species, active nitrogen species, hydrogen peroxide, bio-ions and free radicals, but the dopant may be a hydrogen ion in terms of the fact that it can further improve infrared light absorption performance and electrical conductivity of the conjugated polymer. The amphiphile polymer surrounds particles including a mixture of the conjugated polymer and the fatty acid, to impart hydrophilicity to the conjugated polymer nanoparticles. As a result, the conjugated polymer nanoparticles may have a core-shell structure which includes a core including the conjugated polymer and the fatty acid, and a shell including the amphiphile polymer surrounding the core. Meanwhile, the core may be a mixture of the conjugated polymer and the fatty acid, while the core may have a layered structure in which the conjugated polymer is surrounded by the fatty acid.

Any amphiphile polymer may be used without limitation so long as it has a hydrophilic group and a hydrophobic group and the amphiphile polymer may be chemically synthesized or naturally derived. In addition, the amphiphile polymer may be a cationic surfactant, an anionic surfactant, an amphoteric surfactant, a nonionic surfactant or a mixture thereof.

Specifically, the amphiphile polymer may be sodium cholate hydrate, n-octyl glucoside, octyl thioglycoside, N-octanoyl-N-methylglucamine, N-nonanoyl-N-methylglucamine, quillaja bark-derived saponin, polyoxyethylene sorbitan monolaurate, sodium dodecyl sulfate, tetramethylammonium hydroxide solution, hexadecyltrimethylammonium bromide (CTAB), didodecyldimethylammonium bromide (DMAB), N,N-bis(3-D-glucoamidopropyl) deoxy-cholamide (deoxy-BIGCHAP), N,N-bis(3-D-glucoamidopropyl) cholamide (BIGCHAP), polyvinyl alcohol, polyethylene glycol dodecyl ether, Pluronic F-68, Triton X-100, Triton X-114, Tween 40, Tween 80, Igepal CA-630, Igepal CO-210, Igepal CO -520, Igepal CO-630, Igepal CO-720, Igepal CO-890, Igepal DM-970, Igepal CA-210, Igepal CA-520, Igepal CA-630, N-decanoyl-N-methylglucamine, nonylphenyl polyethylene glycol, Brij 76, Brij 58, Brij 35P, Brij 30, Polysorbate 80, cyclohexylmethyl-β-D-maltoside (Cymal-1), 2-cyclohexylethyl-β-D-maltoside (Cymal-2), 5-cyclohexylpentyl-β-D-maltoside (Cymal-5), 6-cyclohexylhexyl-β-D-maltoside (Cymal-6), digitonin, decyl-β-D-maltopyranoside, lauryl-β-D-maltoside (DDM), n-hexadecyl-β-D-maltoside, undecyl-β-D-maltoside, decyl-β-D-1-thiomaltopyranoside, decyl-β-D-1-thioglucopyranoside, dimethyldecylphosphine oxide, dodecyldimethylphosphine oxide or a mixture thereof.

The conjugated polymer nanoparticles have infrared light absorption properties when doped even under a neutral environment and are thus applicable as a photothermal therapy material. When the conjugated polymer nanoparticles include a contrast medium material, diagnosis of diseases is possible by near-infrared imaging.

As a specific example, cancer cells can be detected using the conjugated polymer nanoparticles. The majority of cancer cells continue growing and proliferating and the energy required for this growth is obtained by glycolysis. Accordingly, glycolysis more actively occurs and more glycolysis products such as pyruvate and lactic acid are obtained in cancer cells, as compared to in normal cells. That is, when the conjugated polymer nanoparticles are present under environments containing pyruvate and lactic acid, such as cancer cells, the pyruvate and lactic acid serve as dopants and are used to dope the conjugated polymers. Depending on the doping of the conjugated polymer, the absorbance of the conjugated polymer is changed and color is thus changed. Accordingly, using this color change, the conjugated polymer nanoparticles can be used as sensors and kits for detecting cancer cells.

There is no limitation as to the kind of cancer cells that can be detected using the conjugated polymer nanoparticles. For example, cancer cells include rectal cancer, gallbladder cancer, ovarian cancer, colorectal cancer, lymphoma, brain cancer, prostate cancer, malignant melanoma, breast cancer, stomach cancer, lung cancer, ovarian cancer, liver cancer, bronchial cancer, nasopharyngeal cancer, laryngeal cancer, pancreatic cancer, bladder cancer, colon cancer, sarcoma cancer and uterine cancer cells and the like.

Meanwhile, the conjugated polymer nanoparticles may include a pharmaceutically active ingredient, in addition to the conjugated polymer and the fatty acid. The conjugated polymer nanoparticles include the pharmaceutically active ingredient, thereby being useful as a drug delivery material and a disease treatment material.

When the conjugated polymer nanoparticles have the core-shell structure, the pharmaceutically active ingredient can be contained in the core. In this case, the pharmaceutically active ingredient, the conjugated polymer and the fatty acid may be present as a mixture, or the pharmaceutically active ingredient may surround the mixture of the conjugated polymer and the fatty acid in a layer form.

The pharmaceutically active ingredient may be selected from the group consisting of anticancer agents, antibiotics, hormones, hormone antagonists, interleukin, interferon, growth factors, tumor necrosis factors, endotoxins, lymphotoxin, urokinase, streptokinase, tissue plasminogen activators, protease inhibitors, alkylphosphocholines, radioisotope-labeled molecules, cardiovascular drugs, gastrointestinal drugs and neurological drugs.

In particular, examples of the anticancer agents include epirubicin, docetaxel, gemcitabine, paclitaxel, cisplatin, carboplatin, taxol, procarbazine, cyclophosphamide, dactinomycin, daunorubicin, etoposide, tamoxifen, doxorubicin, mitomycin, bleomycin, plicomycin, transplatinum, vinblastin, methotrexate and the like.

The conjugated polymer nanoparticles may include 1 to 1,000 parts by weight of the fatty acid, with respect to 100 parts by weight of the conjugated polymer. When the content of the fatty acid is less than 1 part by weight, an efficiency of loading the pharmaceutical ingredient may be deteriorated and when the content of the fatty acid exceeds 1,000 parts by weight, the size of the conjugated polymer nanoparticles may be excessively large and stability of the conjugated polymer nanoparticles may thus be deteriorated.

The conjugated polymer nanoparticles may include 1 to 1,000 parts by weight of the amphiphile polymer, with respect to 100 parts by weight of the conjugated polymer. When the content of the amphiphile polymer is less than 1 part by weight, the amount of the amphiphile polymer surrounding the conjugated polymer nanoparticles is excessively low and stability of the conjugated polymer nanoparticles in an aqueous phase may be deteriorated and when the content exceeds 1,000 parts by weight, biocompatibility may be deteriorated upon application to in vivo cells, animals and the like.

In the case where the conjugated polymer nanoparticles further include the pharmaceutically active ingredient, the conjugated polymer nanoparticles may include 0.1 to 100 parts by weight of the pharmaceutically active ingredient, with respect to 100 parts by weight of the conjugated polymer. When the content of the pharmaceutically active ingredient is less than 0.1 parts by weight, as the content of the pharmaceutical ingredient is extremely low, there may be problems associated with treatment using the pharmaceutical ingredient, and when the content exceeds 100 parts by weight, fluorescence characteristics such as self-quenching and other optical properties may be deteriorated.

The conjugated polymer nanoparticles may have a diameter of 1 to 500 nm, preferably 5 to 50 nm, more preferably 10 to 25 nm. When the diameter of the conjugated polymer nanoparticles exceeds 500 nm, solubility may be deteriorated and colloid stability in an aqueous solution phase may be lowered due to large particle size.

A method of producing the conjugated polymer nanoparticles according to another embodiment includes dissolving conjugated polymers and fatty acid in a solvent to prepare a first mix solution, mixing the mix solution with a solution containing an amphiphile polymer to prepare a second mix solution, and conducting reaction of the second mix solution. In accordance with the method of producing the conjugated polymer nanoparticles, conjugated polymer nanoparticles doped even under a neutral environment can be produced.

Specifically, the conjugated polymers and the fatty acid are dissolved in an aqueous solvent and the mixture is mixed with an aqueous amphiphile polymer solution. The mixture containing the conjugated polymer, fatty acid and the amphiphile polymer is stirred and purified, thereby producing conjugated polymer nanoparticles. Since the aqueous solvent is spontaneously emulsified in water, the conjugated polymer nanoparticles can be produced without injection of additional energy.

Meanwhile, in order for the conjugated polymer nanoparticles to further include the pharmaceutically active ingredient, in the process of dissolving the conjugated polymers and the fatty acid in the aqueous solvent, the pharmaceutically active ingredient may be further added and be dissolved in the aqueous solvent, in addition to the conjugated polymers and the fatty acid.

In a specific embodiment of the present invention, the conjugated polymer, the fatty acid and the pharmaceutically active ingredient are dispersed in the aqueous solvent, and the conjugated polymer, the fatty acid and the pharmaceutically active ingredient dispersed in the aqueous solvent are injected into an aqueous phase in which an amphiphile polymer is dispersed. After injection, stirring is conducted. As a result, the solvent phase is equilibrated with the aqueous phase in the form of a droplet. At this time, the amphiphile polymer is adsorbed on the droplet, thereby obtaining conjugated polymer nanoparticles.

The conjugated polymer nanoparticles thus obtained may have a structure including a conjugated polymer core and a hydrophilic shell. By the hydrophilic group of the amphiphile polymer, a hydrophilic shell surrounding the conjugated polymer core including the conjugated polymer, the fatty acid and the pharmaceutically active material can be formed. The hydrophilic shell is located outside the conjugated polymer core so that it exerts high water solubility to improve dispersibility of the conjugated polymer nanoparticles.

Any solvent may be used as the aqueous solvent without limitation so long as it is soluble in water. For example, the aqueous solvent may be N-methyl-2-pyrrolidone, acetone, acetonitrile, carbon tetrachloride, chloroform, cyclohexane, 1,2-dichloroethane, dichloromethane, diethyl ether, dimethyl formamide, dimethyl sulfoxide, 1,4-dioxane, ethanol, ethyl acetate, heptane, hexane, methanol, methyl tert-butyl ether, pentane, 1-propanol, 2-propanol, tetrahydrofuran, toluene, 2,2,4-trimethylpentane, water or a mixture thereof.

The conducting reaction of the second mix solution may be carried out by stirring the second mix solution at a temperature lower than or equal to a melting point of the fatty acid. That is, the reaction of the second mix solution is carried out by a temperature lower than or equal to the melting point of the fatty acid, thereby producing conjugated polymer nanoparticles including the fatty acid present in a solid phase. Accordingly, the reaction temperature may be 1 to 99° C., preferably 15 to 50° C., more preferably 30 to 40° C. which is lower than or equal to the melting point of the fatty acid.

EXAMPLES

Hereinafter, certain examples of the present invention will be described in more detail such that a person having ordinary knowledge in the field to which the present invention pertains can easily implement the same.

However, the present invention can be implemented in various forms and should not be construed as being limited to the examples described herein.

Preparation Example: Synthesis of Polyaniline

Preparation Example 1

Emeraldine base (EB) as polyaniline was synthesized in the presence of excess HCl by chemical oxidative polymerization. An aniline monomer (0.2 mol) was added to a 1M HCl aqueous solution (300 mL). Subsequently, an ammonium persulfate solution (0.05 mol) prepared in a 1M HCl aqueous solution (200 mL) as an oxidant was added dropwise to conduct polymerization at room temperature for 6 hours. A dark green precipitated polymer salt (ES) was filtered and the filtrate was collected from a reaction container and was then dispersed again in a 1M NaOH solution (500 mL). Then, dequantized EB was filtered and dispersed again in acetone (500 mL). Finally, the resulting dispersion was dried in a vacuum filtration oven for 48 hours to obtain a fine EB powder.

The molecular weight of EB synthesized using gel permeation chromatography (Acme 9200 GPC, Young Lin Instrument Co., Ltd.) was measured. As a result, the molecular weight was found to be 5,200 Da (dispersion degree: 1.1).

Example: Production of Polyaniline Nanoparticles

Examples 1 to 3: PAniLA 5 mg of the polyaniline prepared in Preparation Example 1, each of 60 mg (100%), 300 mg (500%) and 600 mg (1,000%) of lauric acid and 1 mg of doxorubicin were dissolved in 4 mL of N-methyl-2-pyrrolidone, and the mixture 1 was added to 20 mL of an aqueous solution containing 100 mg of Tween 80. The mixture 2 was reacted under stirring at room temperature for 4 hours and dialysis was conducted using a dialysis membrane with Mw of 3,000 for 24 hours. After dialysis, the mixture 3 was centrifuged three times at 3,000 rpm for 60 minutes and was then dispersed in 5 mL of phosphate buffered saline (PBS).

Example 4: PAniLA 5 mg of the polyaniline prepared in Preparation Example 1 and 60 mg of lauric acid were dissolved in 4 mL of N-methyl-2-pyrrolidone and the mixture 1 was added to 20 mL of an aqueous solution containing 100 mg of Tween 80. The mixture 2 was reacted under stirring at room temperature for 4 hours and dialysis was conducted using a dialysis membrane with Mw of 3,000 for 24 hours. After dialysis, the mixture 3 was centrifuged three times at 3,000 rpm for 60 minutes and was then dispersed in 5 mL of phosphate buffered saline (PBS).

Examples 5 to 7: PAniLA

Polyaniline nanoparticles were produced in the same manner as in Example 4, except that oleic acid, capric acid and caprylic acid were each used instead of the lauric acid.

Reference Example 1: TPAni 10 mg of polyaniline prepared in Preparation Example 1 was dissolved in 1.5 mL of N-methyl-2-pyrrolidone and the mixture was added to 20 mL of an aqueous solution containing 200 mg of Tween 80. The mixture was reacted under vigorous stirring at room temperature for 4 hours. After dialysis, the mixture was centrifuged three times at 1,500 rpm for 30 minutes and Tween 800-coated polyaniline nanoparticles (TPAni) were purified and dispersed in an aqueous phase.

Test Example 1: Characterization of Polyaniline Nanoparticles

FIG. 1 is a transmission electron microscopy (TEM; JEM-1011 JEOL, Japan) image of polyaniline nanoparticles produced in Example 1. As can be seen from FIG. 1, the produced polyaniline nanoparticles have a structure in which lauric acid surrounds polyaniline as a core.

In addition, it can be seen from the transmission electron microscopy image that the polyaniline nanoparticles have a particle diameter of about 50 to 60 nm.

Test Example 2: Evaluation of Absorbance Properties and Photothermal Properties of Polyaniline Nanoparticles FIGS. 2A and 2B are graphs showing absorbance properties of polyaniline nanoparticles produced in Examples 1 to 3.

Figure 2A:
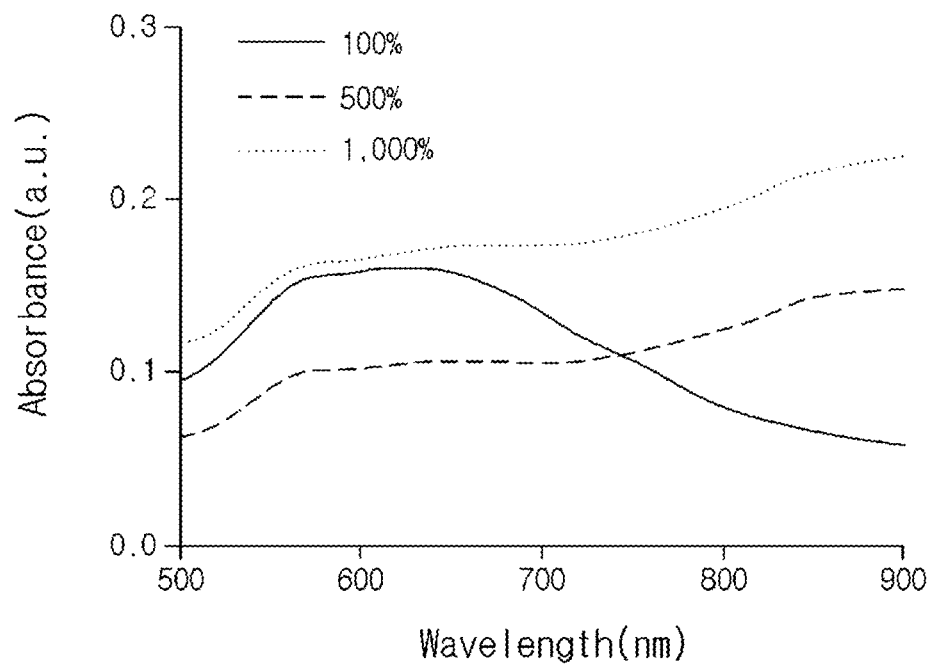
FIGS. 2A and 2B are graphs showing absorbance properties of polyaniline nanoparticles produced in Examples 1 to 3.

As can be seen from FIG. 2A, observation results of absorbance properties of Example 1 (the content of lauric acid: 100%), Example 2 (the content of lauric acid: 500%) and Example 3 (the content of lauric acid: 1,000%) show that under the condition of 100% lauric acid, doping is not observed in an image (green-blue) visible by the naked eye and an absorption spectrum (peak occurs in a 600 nm region) under neutral conditions, whereas, as the content of lauric acid increases, doping occurs even under neutral conditions (solution color: green, absorption peak: 900 nm).

Figure 2B:
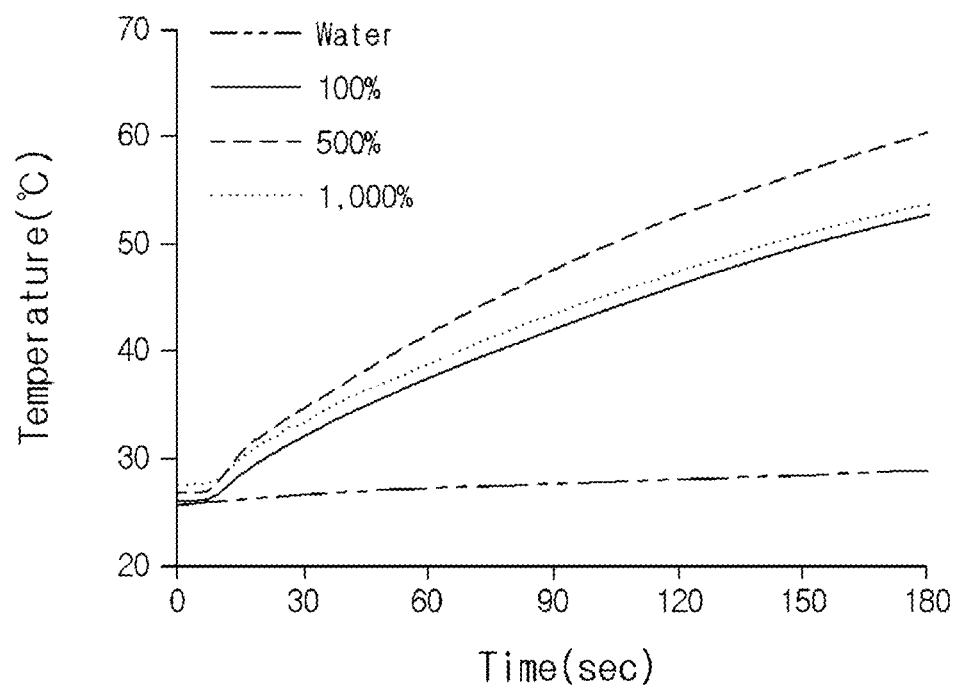

In addition, as can be seen from FIG. 2B, polyaniline nanoparticles produced in Examples 1 to 3 exert a photothermal effect in which heat is emitted by light absorption. In particular, the temperature increment is the highest under the condition of 500% lauric acid (Example 2: 300 mg).

Meanwhile, the polyaniline nanoparticles produced in Examples 4 to 7 can exhibit similar absorbance properties and photothermal properties to polyaniline nanoparticles produced in Example 1.

Test Example 3: Evaluation of Fluorescence Characteristics of Polyaniline Nanoparticles FIG. 3 is a graph showing fluorescence characteristics of polyaniline nanoparticles (100%, 500% and 1,000%) produced in Examples 1 to 3 and doxorubicin (DOX).

Figure 3:
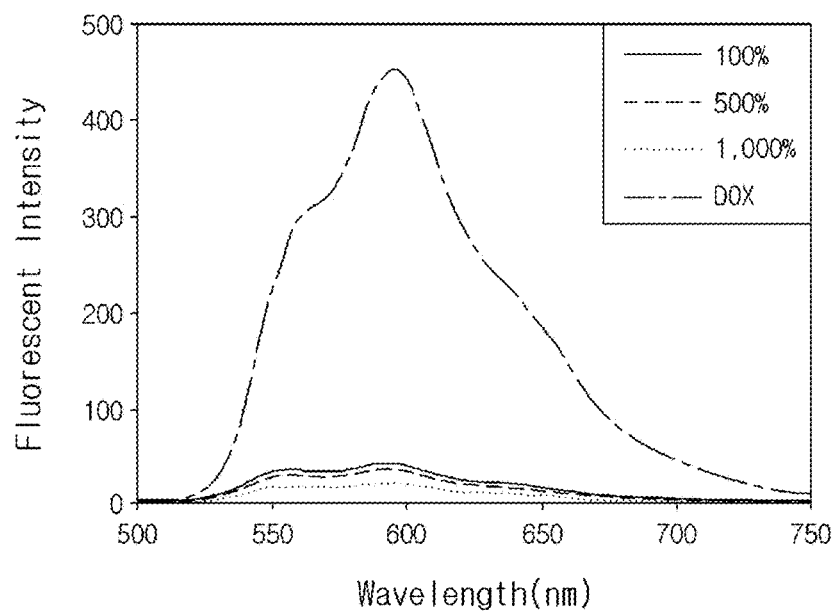
FIG. 3 is a graph showing fluorescence characteristics of polyaniline nanoparticles (100%, 500% and 1,000%) produced in Examples 1 to 3 and doxorubicin (DOX)

That is, FIG. 3 shows fluorescent signals of doxorubicin (DOX) as a drug having fluorescent properties and polyaniline nanoparticles produced in Examples 1 to 3 containing doxorubicin. As can be seen from FIG. 3, when polyaniline nanoparticles are produced from increased amounts of lauric acid in order of 100% (60 mg), 500% (300 mg) and 1,000% (600 mg), fluorescent signal of doxorubicin is significantly decreased.

This is due to absorbance properties of the polyaniline nanoparticles, more specifically, the fact that, since polyaniline nanoparticles having a peak near 600 nm entirely absorb fluorescent emitting signals of doxorubicin, almost no fluorescent signals are measured after particle synthesis.

The results indicate that doxorubicin is encapsulated in the polyaniline nanoparticles and multiple materials such as lauric acid and doxorubicin can be loaded in the polyaniline nanoparticles.

Test Example 4: Evaluation of Photothermal Therapy Effect of Polyaniline Nanoparticles FIG. 4A shows a dark field image for confirming uptake of polyaniline nanoparticles produced in Example 4 and Reference Example 1 into cells, after culturing the polyaniline nanoparticles in the cells for 48 hours, and FIG. 4B shows a photothermal therapy effect after conducting laser irradiation to polyaniline nanoparticles up-taken into the cells.

Figure 4:
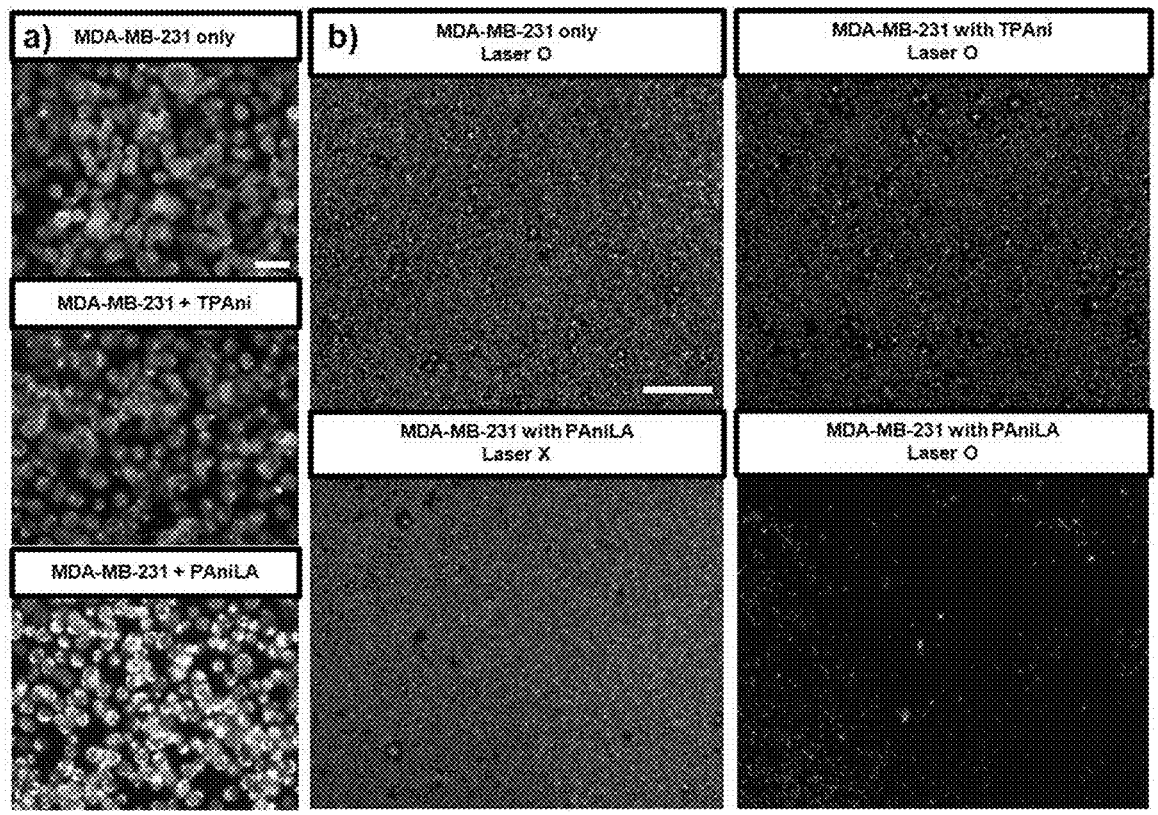
FIG. 4A shows a dark field image for confirming uptake of polyaniline nanoparticles produced in Example 4 and Reference Example 1 into cells, after culturing the polyaniline nanoparticles in the cells for 48 hours.
FIG. 4B shows photothermal therapy effects after conducting laser irradiation on polyaniline nanoparticles up-taken into the cells.

In FIG. 4A, "MDA-MB-231 only" represents a case where only breast cancer cell lines are cultured, "MDA-MB-231+TPAni" represents a case where breast cancer cell lines are cultured together with polyaniline nanoparticles produced in Reference Example 1, and "MDA-MB -231+ PAniLA" represents a case where breast cancer cell lines are cultured together with the polyaniline nanoparticles produced in 4.

As can be seen from FIG. 4A, more polyaniline nanoparticles (PAniLA) produced in Example 4 are up-taken into MDA-MB-231 breast cancer cell lines, as compared to the polyaniline nanoparticles produced in Reference Example 1 (TPAni). For reference, white glittering parts represent PAniLA particles.

FIG. 4B shows results confirming photothermal therapy effects after up-take of polyaniline nanoparticles into cells and then laser irradiation (green-blue parts represent living cells). In FIG. 4B, "MDA-MB-231 only Laser O" represents a case where only MDA-MB-231 cells are subjected to laser irradiation, "MDA-MB-231 with TPAni Laser O" represents a case where both breast cancer cell lines and the polyaniline nanoparticles produced in Reference Example 1 having been cultured together are subjected to laser irradiation, "MDA- MB-231 with PAniLa Laser X" represents a dark field image showing, before laser irradiation, a case where both breast cancer cell lines and the polyaniline nanoparticles produced in Example 4 are cultured together, and "MDA-MB-231 with PAniLa Laser O" represents a dark field image showing, after laser irradiation, a case where both breast cancer cell lines and the polyaniline nanoparticles produced in Example 4 are cultured together.

As can be seen from FIG. 4B, when only MDA-MB-231 cells are subjected to laser irradiation (MDA-MB-231 only Laser O), there is no impact on cells. When laser irradiation is conducted after uptake of the polyaniline nanoparticles produced in Reference Example 1 into the cells (MDA-MB-231 with TPAni Laser O), there is slight damage to cells. The cells in which the polyaniline nanoparticles produced in Example 4 (MDA-MB-231 with PAniLa Laser X) are up-taken have almost no damage, and the polyaniline nanoparticles produced in Example 4 have no toxicity. When laser irradiation is conducted after uptake of the polyaniline nanoparticles produced in Example 4 into the cells (MDA-MB-231 with PAniLa Laser O), there is almost no living cell. The reason for this is that the polyaniline nanoparticles produced in Example 4 absorb light emitted from the laser, thus emitting heat based on the photothermal effect. The emitted heat eliminates cells.

Figure 5:
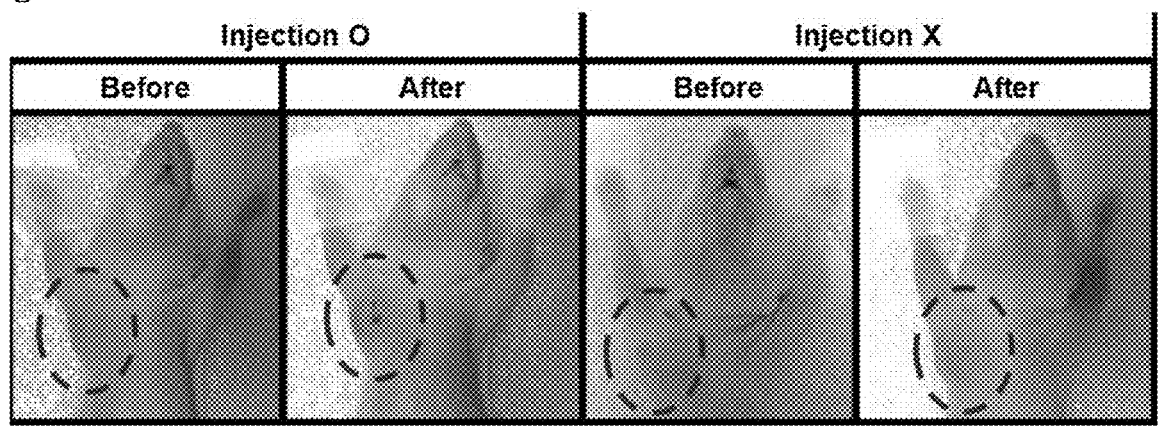
FIG. 5 is an image showing results of laser irradiation conducted after injection, into a mouse model, of MDA-MB-231 breast cancer cell lines cultured together with the polyaniline nanoparticles produced in Example 4.

Meanwhile, FIG. 5 is an image showing results of laser irradiation conducted after injection, into a mouse model, of MDA-MB-231 breast cancer cell lines cultured together with the polyaniline nanoparticles produced in Example 4 in order to measure photothermal therapy effect of the polyaniline nanoparticles.

In FIG. 5, "Injection O-Before" represents an image showing after injection, into a mouse model, of MDA-MB-231 breast cancer cell lines cultured together with the polyaniline nanoparticles produced in Example 4 and before laser irradiation, and "Injection O-After" represents an image showing after injection, into a mouse model, of MDA-MB-231 breast cancer cell lines cultured together with the polyaniline nanoparticles produced in Example 4 and then laser irradiation, "Injection X-Before" represents an image showing after injection, into a mouse model, of only MDA-MB-231 breast cancer cell lines before laser irradiation, and "Injection X-After" represents an image showing after injection, into a mouse model, of only MDA-MB-231 breast cancer cell lines and then laser irradiation.

As can be seen from FIG. 5, when MDA-MB-231 breast cancer cell lines cultured together with the polyaniline nanoparticles produced in Example 4 are up-taken into a mouse model and then subjected to laser irradiation, the laser irradiation-applied areas entirely burn black, while, when only the MDA-MB-231 breast cancer cell lines are up-taken into a mouse model and then subjected to laser irradiation, this phenomenon does not occur.

Meanwhile, the polyaniline nanoparticles produced in Examples 5 to 7 exhibit similar photothermal therapy effects to the polyaniline nanoparticles produced in Example 4.

Test Example 5: Color Change Behaviors Depending on Acidity of Polyaniline Nanoparticles In order to evaluate color change behaviors depending on acidity of the polyaniline nanoparticles produced in Example 1 and Reference Example 1, polyaniline nanoparticles produced in Example 1 and Reference Example 1 were doped with a variety of concentrations ($10^{-1}$ M to $10^{-10}$ M) of hydrogen chloride (HCl). Then, color change was observed by the naked eye and absorbance was analyzed with an absorption spectrometer (Mecasys UV-2120, Korea). Results are shown in FIG. 6.

Figure 6:
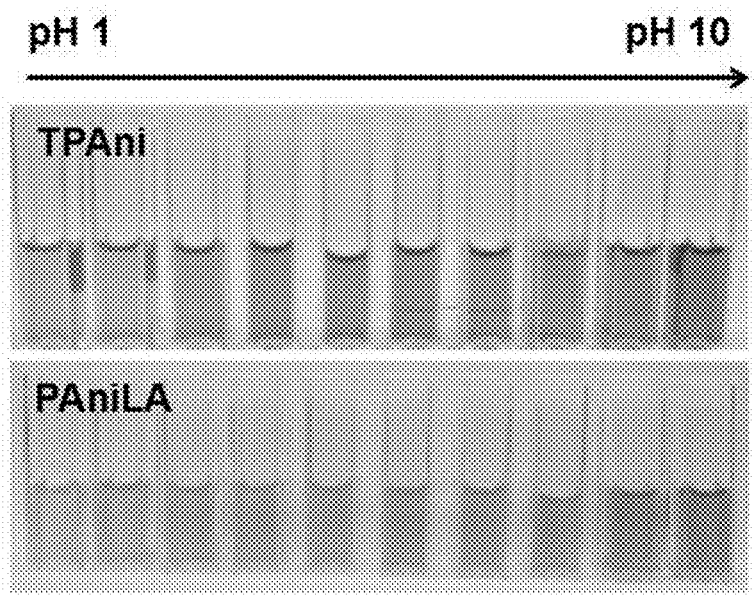
FIG. 6 shows color change behaviors of polyaniline nanoparticles produced under different concentrations of HCl in Example 1 and Reference Example 1.

As can be seen from FIG. 6, the polyaniline nanoparticles produced in Reference Example 1 (TPAni) shift to an emeraldine salt (ES) and thus turn green in the presence of HCl having a higher concentration than $10^{-2}$ M, but shift to an emeraldine base (EB) and thus turn blue in the presence of HCl having a lower concentration than $10^{-3}$ M. On the other hand, the polyaniline nanoparticles produced in Example 1 (PAniLA) shift to an emeraldine salt (ES) and turn green even in the presence of HCl having a lower concentration than $10^{-8}$ M, that is, under a neutral environment, as well as in the presence of HCl having a higher concentration than $10^{-2}$ M.

Meanwhile, like the polyaniline nanoparticles produced in Example 1, the polyaniline nanoparticles produced in Example 4 to 7 can be doped even in the presence of HCl having a lower concentration than $10^{-8}$ M, that is, under a neutral environment, as well as in the presence of HCl having a higher concentration than $10^{-2}$ M.

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

When the conjugated polymer nanoparticles of the present invention are loaded in drugs, the loaded drugs can be released by inducing local temperature changes with a laser, so that accurate drug delivery to local sites, disease diagnosis, disease treatment, near-infrared imaging and photothermal therapy are possible.

The invention claimed is:

1. Conjugated polymer nanoparticles for photothermal therapy comprising:
    a core consisting of a mixture of a conjugated polymer and a fatty acid, and a pharmaceutically active ingredient; and
    a shell surrounding the core and comprising an amphiphile polymer, wherein:
    the fatty acid is selected from the group consisting of oleic acid, capric acid, caprylic acid, palmitic acid, lauric acid, myristic acid, arachidic acid, behenic acid, lignoceric acid, cerotic acid and combinations thereof,
    the conjugated polymer is capable of being doped in the presence of HCl having a lower concentration than $10^{-3}$ M,
    the fatty acid is a phase change material which is present in a solid phase during production of the conjugated polymer nanoparticles and is adapted to be melted by heat emitted from the conjugated polymer absorbing light, and
    the conjugated polymer of the conjugated polymer nanoparticles is capable of being doped at pH 1 to 8 with a dopant.

2. The conjugated polymer nanoparticles for photothermal therapy according to claim 1, wherein the conjugated polymer nanoparticles comprise 1 to 1,000 parts by weight of the fatty acid and 1 to 1,000 parts by weight of the amphiphile polymer, with respect to 100 parts by weight of the conjugated polymer.

3. The conjugated polymer nanoparticles for photothermal therapy according to claim 1, wherein the amphiphile polymer comprises any one selected from the group consisting of a cationic surfactant, an anionic surfactant, an amphoteric surfactant, a nonionic surfactant and a mixture thereof.

4. The conjugated polymer nanoparticles for photothermal therapy according to claim 3, wherein the amphiphile polymer comprises any one selected from the group consisting of sodium cholate hydrate, n-octyl glucoside, octyl thioglycoside, N-octanoyl-N-methylglucamine, N-nonanoyl-N-methylglucamine, quillaja bark-derived saponin, polyoxyethylene sorbitan monolaurate, sodium dodecyl sulfate, tetramethylammonium hydroxide solution, hexadecyltrimethylammonium bromide (CTAB), didodecyldimethylammonium bromide (DMAB), N,N-bis(3-D-glucoamidopropyl)deoxy -cholamide (deoxy-BIGCHAP), N,N-bis(3-D-glucoamidopropyl)cholamide (BIGCHAP), polyvinyl alcohol, polyethylene glycol dodecyl ether, N-decanoyl-N-methylglucamine, nonylphenyl polyethylene glycol, Polysorbate 80, cyclohexylmethyl-β-D-maltoside (Cymal-1), 2-cyclohexylethyl-β-D-maltoside (Cymal-2), 5-cyclohexylpentyl-β-D-maltoside (Cymal-5), 6-cyclohexylhexyl-β-D-maltoside (Cymal-6), digitonin, decyl-β-D-maltopyranoside, lauryl-β-D-maltoside (DDM), n-hexadecyl-β-D-maltoside, undecyl-β-D-maltoside, decyl-β-D-1-thiomaltopyranoside, decyl-β-D-1-thioglucopyranoside, dimethyldecylphosphine oxide, dodecyldimethylphosphine oxide and a mixture thereof.

5. The conjugated polymer nanoparticles for photothermal therapy according to claim 1, wherein the conjugated polymer comprises any one selected from the group consisting of polyacetylene, polyaniline, polypyrrole, polythiophene, poly(1,4-phenylenevinylene), poly(1,4-phenylene sulfide), poly(fluorenyleneethynylene), a derivative thereof and a mixture thereof.

6. The conjugated polymer nanoparticles for photothermal therapy according to claim 1, wherein the conjugated polymer nanoparticles comprise 0.1 to 100 parts by weight of the pharmaceutically active ingredient, with respect to 100 parts by weight of the conjugated polymer.

7. The conjugated polymer nanoparticles for photothermal therapy according to claim 1, wherein the pharmaceutically active ingredient comprises any one selected from the group consisting of anticancer agents, antibiotics, hormones, hormone antagonists, interleukins, interferons, growth factors, tumor necrosis factors, endotoxins, lymphotoxins, urokinase, streptokinase, tissue plasminogen activators, protease inhibitors, alkylphosphocholine, radioisotope-labeled molecules, cardiovascular drugs, gastrointestinal drugs and neurological drugs.

8. The conjugated polymer nanoparticles for photothermal therapy according to claim 1, wherein the conjugated polymer nanoparticles have a diameter of 1 to 500 nm.

9. A method of producing conjugated polymer nanoparticles for photothermal therapy comprising:
dissolving a conjugated polymer and fatty acid in a solvent to prepare a first mix solution;
mixing the first mix solution with a solution containing an amphiphile polymer to prepare a second mix solution; and
conducting reaction of the second mix solution,
wherein the conjugated polymer nanoparticles comprise a core consisting of the mixture of the conjugated polymer and the fatty acid, and a pharmaceutically active ingredient; and a shell surrounding the core and comprising the amphiphile polymer, and
wherein:
the fatty acid is selected from the group consisting of oleic acid, capric acid, caprylic acid, palmitic acid, lauric acid, myristic acid, arachidic acid, behenic acid, lignoceric acid, cerotic acid, and combinations thereof,
the conjugated polymer is capable of being doped in the presence of HCl having a lower concentration than $10^{-3}$ M,
the fatty acid is a phase change material which is present in a solid phase during the production of the conjugated polymer nanoparticles and can be melted by heat emitted from the conjugated polymer absorbing light, and
the conjugated polymer of the conjugated polymer nanoparticles is capable of being doped at pH 1 to 8 with a dopant.

10. The method according to claim 9, wherein the preparing the first mix solution comprises further adding a pharmaceutically active ingredient.

11. The method according to claim 9, wherein the solvent comprises any one selected from the group consisting of N-methyl-2-pyrrolidone, acetone, acetonitrile, carbon tetrachloride, chloroform, cyclohexane, 1,2-dichloroethane, dichloromethane, diethyl ether, dimethyl formamide, dimethyl sulfoxide, 1,4-dioxane, ethanol, ethyl acetate, heptane, hexane, methanol, methyl tert-butyl ether, pentane, 1-propanol, 2-propanol, tetrahydrofuran, toluene, 2,2,4-trimethylpentane, water and a mixture thereof.

12. The method according to claim 9, wherein the reaction of the second mix solution is conducted by stirring the second mix solution at a temperature lower than or equal to a melting point of the fatty acid.

* * * * *